(12) United States Patent
Yoshida

(10) Patent No.: US 9,289,117 B2
(45) Date of Patent: Mar. 22, 2016

(54) OPTICAL TOMOGRAPHIC IMAGING APPARATUS

(71) Applicant: CANON KABUSHIKI KAISHA, Tokyo (JP)

(72) Inventor: Hirofumi Yoshida, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 143 days.

(21) Appl. No.: 14/263,804

(22) Filed: Apr. 28, 2014

(65) Prior Publication Data

US 2014/0320812 A1 Oct. 30, 2014

(30) Foreign Application Priority Data

Apr. 30, 2013 (JP) .................. 2013-095623

(51) Int. Cl.
*A61B 3/14* (2006.01)
*A61B 3/10* (2006.01)

(52) U.S. Cl.
CPC ..................... *A61B 3/102* (2013.01)

(58) Field of Classification Search
USPC .................................................. 351/206, 208
See application file for complete search history.

(56) References Cited

U.S. PATENT DOCUMENTS 5,537,162 A 7/1996 Hellmuth et al.

FOREIGN PATENT DOCUMENTS

JP 2011-11052 A 1/2011

*Primary Examiner* — Jack Dinh
(74) *Attorney, Agent, or Firm* — Canon USA Inc. IP Division

(57) ABSTRACT

An optical tomographic imaging apparatus includes a first lens, a second lens and a scanning unit on an optical path of measurement light that irradiates an object to be examined. The second lens has a focal length longer than a focal length of the first lens. A portion of the object to be examined is disposed at a focal position of the first lens, and the scanning unit is disposed at a focal position of the second lens. The scanning unit scans the measurement light via the second lens with a smaller angle than an angle at which the measurement light irradiates the object to be examined via the first lens.

8 Claims, 6 Drawing Sheets

OPTICAL TOMOGRAPHIC IMAGING APPARATUS

BACKGROUND OF THE INVENTION

1. Field of the Invention

The present invention relates to an optical tomographic imaging apparatus for use in an ophthalmologic medical care and the like.

2. Description of the Related Art

Currently, various ophthalmologic apparatuses using optical apparatuses are known. For example, various apparatuses such as an anterior eye portion imaging apparatus, a fundus camera, and a confocal scanning laser ophthalmoscope (SLO) are used as optical apparatuses for observing a subject's eye (an eye to be examined). Among them, an optical tomographic imaging apparatus based on optical coherence tomography (OCT) utilizing multi-wavelength lightwave interference is an apparatus that can acquire a tomographic image of a sample at a high resolution, and is becoming an apparatus essential for clinics specialized in retinas as an ophthalmologic apparatus. Hereinafter, this apparatus will be referred to as an OCT apparatus.

The OCT apparatus emits measurement light, which is low-coherent light, to the sample (subject's eye or part thereof), and can measure backscattering light from this sample at a high sensitivity by using an interference system or an interference optical system. The low-coherent light is characterized in that a tomographic image can be acquired at a high resolution by increasing a wavelength width thereof. Further, the OCT apparatus can acquire a tomographic image at a high resolution by scanning the measurement light on the sample. Therefore, the OCT apparatus can acquire a tomographic image of a retina on a fundus of a subject's eye, and is widely used for ophthalmologic examination or diagnosis of a retina or the like.

Generally, the OCT apparatus as an ophthalmologic apparatus is provided with a fundus observation optical system, an anterior eye observation optical system, and the like for an alignment adjustment between the apparatus and the subject's eye. The OCT apparatus is constructed by using light beams having different wavelengths in the respective optical systems and separating the wavelengths with use of a wavelength separation unit such as a dichroic mirror, to allow the OCT apparatus to be used together with these optical systems.

Now, suppose that a light source for OCT emits light having a central wavelength of 855 nm, and a wavelength band from approximately 805 nm to approximately 905 nm with a wavelength bandwidth of approximately 100 nm. On the other hand, a light source for OCT discussed in Japanese Patent Application Laid-Open No. 2011-11052 emits light having a central wavelength of 840 nm, and a wavelength band from approximately 815 nm to approximately 865 nm with a wavelength bandwidth of approximately 50 nm. Further, suppose that a light source configured to produce light having a wavelength of 780 nm is used as a light source of an SLO. In this case, an interval between the wavelength of the light source of the SLO and an end of the wavelength band of the light source for OCT is approximately 35 nm (815 nm−780 nm) in the technique discussed in Japanese Patent Application Laid-Open No. 2011-11052. On the other hand, in the case where the wavelength bandwidth is approximately 100 nm, this interval is approximately 25 nm (805 nm−780 nm). In this manner, in the case of the wavelength bandwidth of approximately 100 nm, the wavelength bandwidth of the light source for OCT is wider than that of the technique discussed in Japanese Patent Application Laid-Open No. 2011-11052, thereby leading to a reduction in the interval between the wavelength of the light source of the SLO and the end of the wavelength band of the light source for OCT.

SUMMARY OF THE INVENTION

According to an aspect of the present invention, an optical tomographic imaging apparatus, which is configured to acquire a tomographic image of an object to be examined based on light produced by combining return light from the object to be examined irradiated with measurement light via a first lens and reference light corresponding to the measurement light. The optical tomographic imaging apparatus includes a first scanning unit disposed on an optical path of the measurement light and configured to scan the measurement light on the object to be examined in a first direction, a second scanning unit disposed on the optical path of the measurement light and configured to scan the measurement light in a second direction intersecting with the first direction, a second lens disposed on the optical path of the measurement light between the first lens and the first and second scanning units, the second lens having a longer focal length than a focal length of the first lens, and an optical path branching unit disposed between the first lens and the second lens and configured to branch the optical path of the measurement light to form an observation optical path for observing the object to be examined therefrom. A focal position of the second lens is disposed substantially halfway between the first and second scanning units. The first and second scanning units scan the measurement light via the second lens at a smaller angle than an angle at which the object to be examined is irradiated with the measurement light via the first lens.

Further features of the present invention will become apparent from the following description of exemplary embodiments with reference to the attached drawings.

DESCRIPTION OF THE EMBODIMENTS

Conventionally, a change in an incident angle of measurement light to a dichroic mirror has led to a change in a wavelength separation characteristic (a wavelength band of light transmittable through the dichroic mirror). Therefore, if a low-coherent light source configured to emit light having a wider wavelength bandwidth than that of a conventional technique is used as a light source for OCT, the accuracy for wavelength separation should be further improved compared to the conventional technique because of a shorter interval between a wavelength of a light source of an SLO and an end of the wavelength band of the light source for OCT.

According to an exemplary embodiment of the present invention, an optical tomographic imaging apparatus includes a scanning unit disposed on an optical path of measurement light with which an object to be examined is irradiated via a first lens, and a second lens disposed between the scanning unit and the first lens. Then, the second lens and the scanning unit are disposed in such a manner that an angle at which the measurement light scanned by the scanning unit is incident on an optical path branching unit is substantially maintained. For example, the scanning unit is disposed at a substantially focal position of the second lens. As a result, even when the measurement light is scanned by the scanning unit, it is possible to reduce a change in a wavelength separation characteristic of the optical path branching unit. Therefore, even if a low-coherent light source configured to emit light having a wider wavelength bandwidth than that of the conventional technique is used as the light source for OCT, it is possible to improve the accuracy of wavelength separation for separating the wavelength of the light source for OCT and the wavelength of the light source of the SLO. For example, it is possible to reduce a variation in a transmittance (or a reflectance) of a predetermined wavelength to be separated by the dichroic mirror, which occurs due to a difference in the angle at which the measurement light is incident on the dichroic mirror. The wavelength separation characteristic refers to a ratio between wavelength transmission to wavelength reflection.

Figure 5:
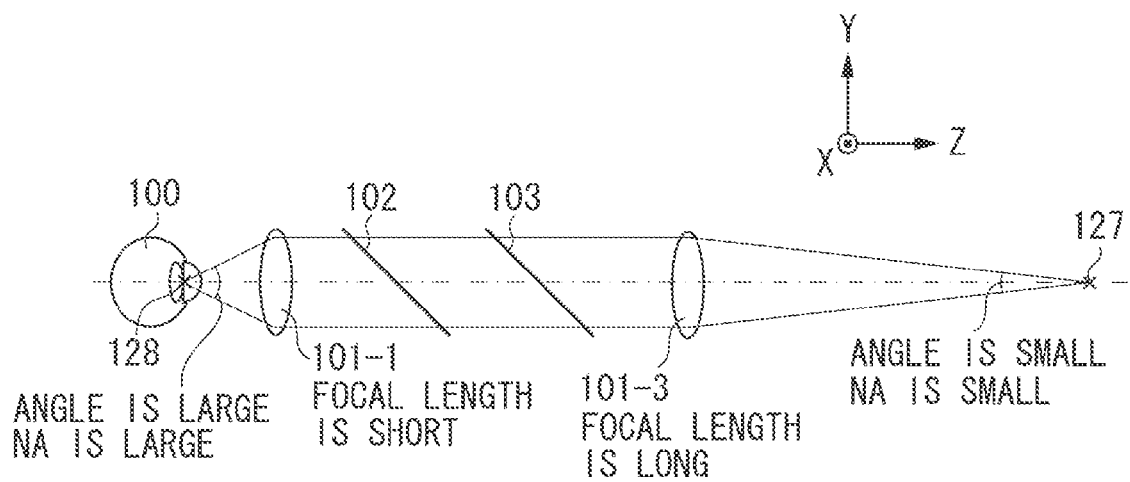
FIG. 5 illustrates that the X and Y scanners scan the measurement light at a smaller angle than an angle at which an object to be examined is irradiated with the measurement light via an objective lens in the optical tomographic imaging apparatus according to the exemplary embodiment of the present invention.

Now, it is desirable that the scanning unit such as a galvanometer mirror is disposed at a position (a position labeled as 127 in FIG. 5) optically conjugate with an anterior eye portion as illustrated in FIG. 5, to reduce vignetting of the measurement light on the anterior eye portion (a pupil position 128) of a subject's eye 100. FIG. 5 illustrates that X and Y scanners scan the measurement light with a smaller angle than an angle at which the object to be examined is irradiated with the measurement light via an objective lens. In this regard, if the measurement light is scanned two-dimensionally in X and Y directions, generally, the X scanner, which is an example of a first scanning unit, and the Y scanner, which is an example of a second scanning unit, are used. In this case, placing both the X scanner and the Y scanner at the optically conjugate position results in an increase in the size of the optical system, and thus an increase in the overall size of the apparatus. Therefore, generally, for example, the X scanner is placed at the optically conjugate position, and the Y scanner is placed so as to be spaced apart therefrom to a degree in which the Y scanner does not contact the X scanner. In this case, the position of the Y scanner does not correspond to the position optically conjugate with the anterior eye portion. Therefore, according to the offset of the scanner from the position optically conjugate with the anterior eye portion, an illumination position is also offset on the anterior eye portion side, whereby vignetting may occur on the anterior eye portion. Further, even if the position optically conjugate with the anterior eye portion coincides with a central position 127 between the X and Y scanners, as will be described below, the illumination position is similarly offset on the anterior eye portion side, whereby vignetting may still occur on the anterior eye portion.

The offset on the scanner side appears as an offset on the anterior eye portion side due to a relationship of axial magnification. Therefore, as the first and second lenses, a lens 101-3, which is an example of the second lens, should have a longer focal length than a focal length of a lens 101-1, which is an example of the first lens, to reduce the offset on the anterior eye portion side. For example, it is desirable that the focal length of the lens 101-1, which is an example of the first lens, is approximately 45 mm and the focal length of the lens 101-3, which is an example of the second lens, is 112.5 mm, i.e., the focal length of the second lens is 2.5 times as long as that of the first lens. Then, as described above, the first scanning unit and the second scanning unit should be disposed at the substantially focal position of the second lens to substantially maintain the angle at which the measurement light scanned by the scanning unit is incident on a second dichroic mirror 103 (or a first dichroic mirror 102), which is an example of the optical path branching unit. As a result, the first and second scanning units are configured to scan the measurement light at a smaller angle than the angle at which the subject's eye is irradiated with the measurement light via the first lens. The above-described "angle" refers to an angle from an optical axis on the optical path of the measurement light. For example, when capturing an image of a fundus in a range of field of 10 mm×10 mm, the range of angle of the subject's eye irradiated with the measurement light is approximately ±17 degrees (total 34 degrees), and the range of scanning angle of the measurement light by X and Y scanners is approximately ±6.8 degrees (total 17 degrees, i.e., approximately 2.5 times). However, the ranges of these angles may desirably be changed according to the range of field to be captured.

Figure 6A:
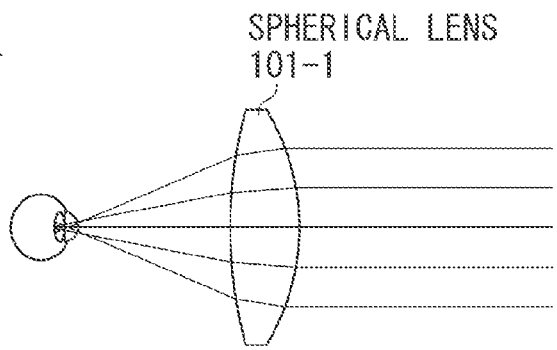
FIGS. 6A, 6B and 6C illustrate exemplary shapes of a first lens.
Figure 6B:
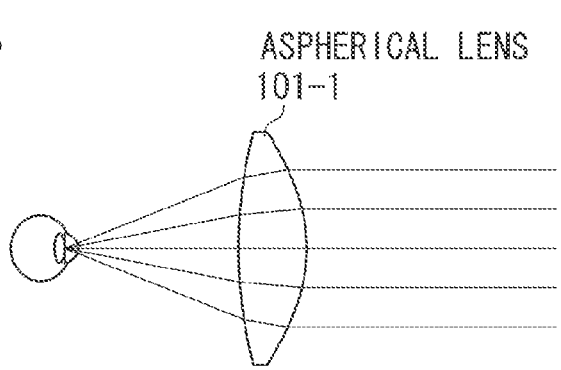
Figure 6C:
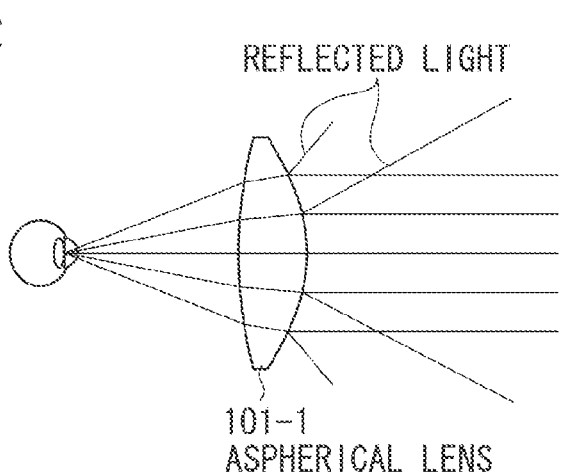
Figure 6D:
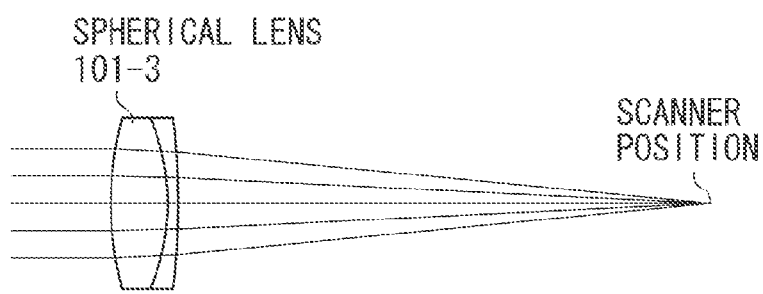
FIG. 6D illustrates exemplary shape of a second lens in the optical tomographic imaging apparatus.

In this configuration, as illustrated in FIG. 6A, spherical aberration easily occurs on the lens 101-1, which is an example of the first lens, compared to the lens 101-3, which is an example of the second lens, because the angle at which the subject's eye is irradiated with the measurement light is larger than the angle at which the measurement light is scanned. Therefore, as illustrated in FIG. 6B, it is desirable that the lens 101-1 is a lens having an aspherical surface to reduce spherical aberration. Then, as illustrated in FIG. 6C, the lens having an aspherical surface can reduce an image of normal reflection because it reflects light entered to the lens surface at a large angle compared to a spherical lens. Further, it is desirable in terms of cost that the lens 101-3 (second lens) on which a spherical aberration unlikely occurs compared to the lens 101-1 is a spherical lens. In this case, as illustrated in FIG. 6D, it is desirable that the lens 101-3 is constructed by joining together a plurality of spherical lenses having different reflective indices. As a result, it is possible to reduce chromatic aberration that occurs on the lens 101-3. As a configuration of cementing a plurality of spherical lenses having different indices, there may be various types of combinations of lenses. For example, among a plurality of spherical lenses, it is desirable to use low-dispersion glass for a convex lens, and to use a high-refractive index and high-dispersion glass for a concave lens.

In the following description, the present exemplary embodiment will be described with reference to the accompanying drawings. The same elements are identified with the same reference numerals throughout the present disclosure.

<Configuration of Apparatus>

Figure 1:
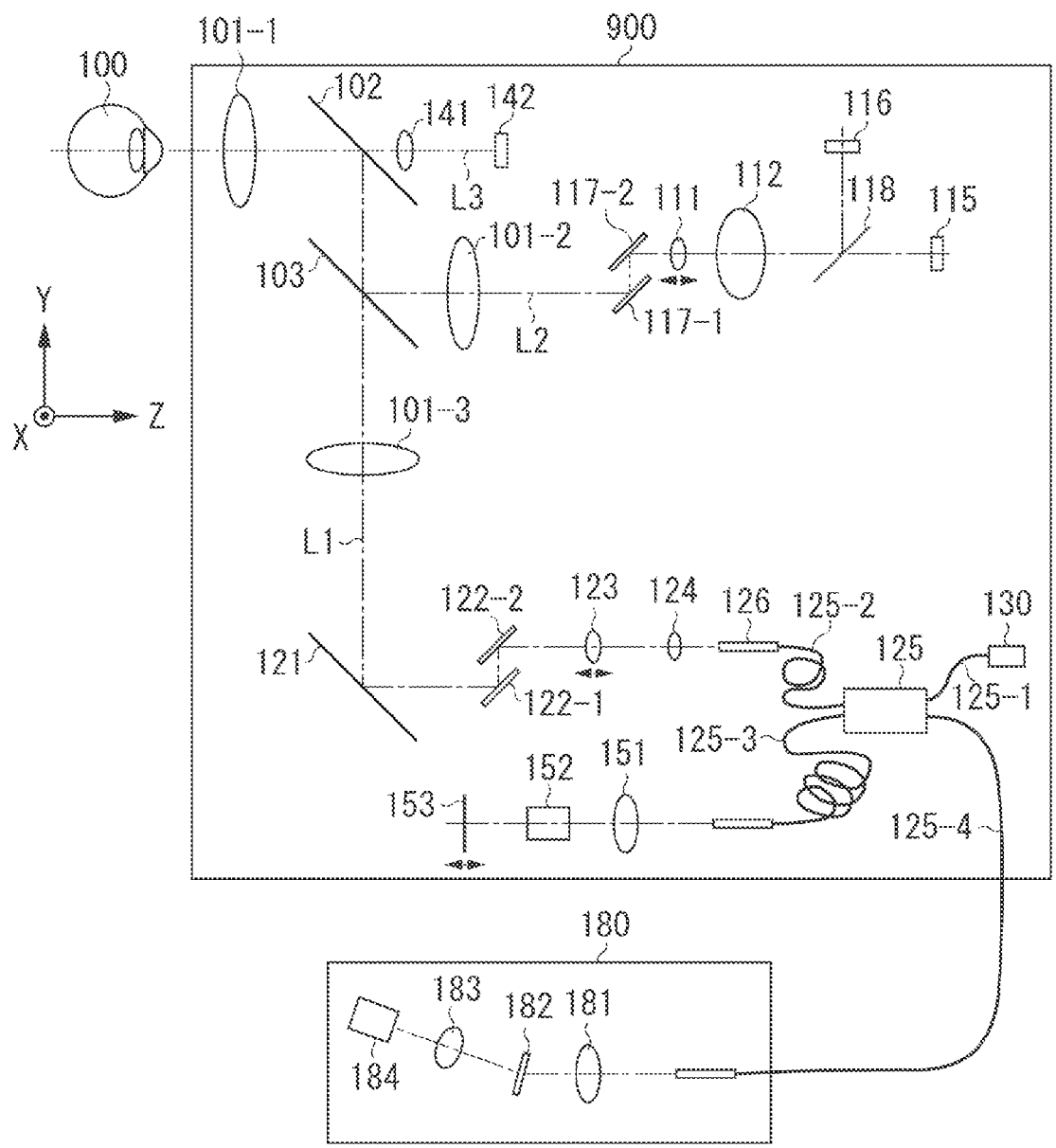
FIG. 1 illustrates an outline of a configuration of an optical tomographic imaging apparatus according to an exemplary embodiment of the present invention.

A configuration of the optical tomographic imaging apparatus (OCT apparatus) according to the present exemplary embodiment will be described with reference to FIG. 1. The optical tomographic imaging apparatus includes an optical head 900 and a spectrometer 180. The optical tomographic imaging apparatus acquires a tomographic image of the object to be examined (subject's eye 100) based on light produced by combining return light from the object to be examined irradiated by the measurement light via the scanning unit, and reference light corresponding to this measurement light.

First, an internal configuration of the optical head 900 will be described. The optical head 900 includes measurement optical systems for capturing an image of an anterior portion of the subject's eye 100, a two-dimensional image of a fundus of the subject's eye 100, and a tomographic image of the subject's eye 100 or a portion thereof. The lens 101-1, which is an objective lens and an example of the first lens, is disposed so as to face the subject's eye 100. Further, an optical path is branched by the first dichroic mirror 102 and the second dichroic mirror 103. The first dichroic mirror 102 and the second dichroic mirror 103 are non-limiting examples of an optical path branching unit. Other examples of the optical path branching unit include a prism, a half-silvered mirror, a half-wave plate, or the like. Regardless of how the optical path branching unit is implemented, the optical path is branched into a measurement optical path L1 of an OCT optical system, a fundus observation optical path and fixation lamp optical path L2, and an anterior eye portion observation optical path L3. These optical paths L1, L2 and L3 are branched according wavelength bands of the measurement light.

<Optical Path L1: Measurement Optical Path of OCT Optical System>

The optical path L1 forms part of the OCT optical system, as described above, and is used to capture a tomographic image of the fundus of the subject's eye 100. More specifically, the optical path L1 is used to acquire an interference signal for forming a tomographic image. The lens 101-3, which is an example of the second lens, a mirror 121, and the scanning unit are disposed on the optical path L1. The scanning unit includes an X scanner 122-1, which is an example of the first scanning unit, and a Y scanner 122-2, which is an example of the second scanning unit. A non-limiting example of the X scanner 122-1 and Y scanner 122-2 includes a scanning galvanometer. One-dimensional (1D) or two-dimensional (2D) galvanometer optical scanners may be used. Other non-limiting examples may include 1D or 2D MEMS (micro-electromechanical mirrors) scanning mirrors. Regardless of implementation, the X scanner 122-1 and the Y scanner 122-2 respectively scan the measurement light on the fundus of the subject's eye 100 in the X direction (a main scanning direction, also referred to as a first direction), and the Y direction (a sub scanning direction, also referred to as a second direction). That is, the X scanner 122-1 scans the measurement light on the fundus of the subject's eye 100 in the first direction and the Y scanner 122-2 scans the measurement light on the fundus of the subject's eye 100 in the second direction intersecting with the first direction. In FIG. 1, for ease of illustration, an optical path between the X scanner 122-1 and the Y scanner 122-2 in parallel with the plane of the sheet of FIG. 1 is shown, but in a real 3-dimensional arrangement, this optical path is formed in a direction perpendicularly to the plane of the sheet of FIG. 1.

<Optical Path L2: Optical System for Fundus Observation>

The optical path L2 is an optical path of an optical system for fundus observation. The optical path L2 is separated, according to the wavelength, from the measurement light of the OCT optical system by the second dichroic mirror 103 (second optical path branching unit). Among a lens 101-2, a focusing lens 111, and a lens 112, the focusing lens 111 is driven along an optical axis thereof by a motor (not-illustrated) for a focusing adjustment for a fixation lamp (not-illustrated) and fundus observation. Movement of the focusing lens 111 is illustrated by a non-labeled double arrow.

First, on the optical path L2, a light source 115 (the light source of the SLO) for fundus observation generates light having a wavelength of 780 nm. Further, an X scanner 117-1, which is an example of a first observation scanning unit, and a Y scanner 117-2, which is an example of a second observation scanning unit, are disposed on the optical path L2 to scan the light emitted from the light source 115 for fundus observation on the fundus of the subject's eye 100. The lens 101-2, which is an example of a third lens, is disposed so as to have a focal position substantially half-way (around a central position) between the X scanner 117-1 and the Y scanner 117-2. The X scanner 117-1 includes, for example, a polygon mirror to scan the light in the X direction at a high speed. Further, the X scanner 117-1 may include a resonant mirror. The Y scanner 117-2 may be implemented in a manner similar to the X scanner 117-1. An optical detector 116 includes, for example, an avalanche photodiode (APD), and it detects light scattered by and reflected from the fundus of the subject's eye 100. A prism 118 is a prism to which a holed mirror or a hollow mirror is evaporated, and separates the illumination light from the light source 115 for fundus observation and the return light from the fundus.

Further, a dichroic mirror (not-illustrated) may be further provided, and a light-emitting diode (LED) or the like may be further provided as a light source of the fixation lamp (not-illustrated). In this case, the light source of the fixation lamp is disposed on the SLO light source side relative to the scanning unit for observation. Due to this arrangement, the scanning unit for observation is also used as a scanning unit for visual fixation, by which a scanning fixation lamp can be formed. In this case, the scanning fixation lamp can work well by using a control unit (not-illustrated) that performs control in such a manner that the light source of the fixation lamp is turned on when light from the light source of the fixation lamp is scanned at a position desired by an examiner. Turning on and turning off the light source of the fixation lamp may be replaced with opening and closing a shutter disposed on the second optical path L2.

The optical path L2 may be a line scanning SLO (a line SLO) that scans a line beam in a single direction by using a cylindrical lens or the like, instead of the above-described point scanning SLO that scans two-dimensionally a spot to acquire a two-dimensional image of the fundus. Further, the optical path L2 may be configured to perform infrared observation by using a two-dimensional charge coupled device (CCD) sensor, instead of using the scanning unit. More specifically, the optical path L2 may be configured to include a CCD sensor for fundus observation, instead of the X scanner 117-1 and the Y scanner 117-2, to acquire a two-dimensional image of the fundus of the subject's eye 100. In this case, the two-dimensional CCD sensor is configured to detect a wavelength of the not-illustrated illumination light for fundus observation, in particular, around 780 nm.

Further, the fixation lamp on the optical path L2 may be configured in such a manner that the examiner prompts visual fixation of an examinee to a desired position by generating visual light by a display for visual fixation such as a liquid-crystal display, and changing a lighting position on the display for visual fixation. In this case, the display for visual fixation is disposed closer to a third dichroic mirror 104 relative to the scanning unit for observation.

<Optical Path L3: Optical System for Anterior Eye Observation>

A lens 141, and an infrared CCD sensor 142 for anterior eye observation are disposed on the optical path L3. The infrared CCD sensor 142 has a sensitivity to a wavelength of not-illustrated illumination light for anterior eye observation, in particular, around 970 nm.

<Position Optically Conjugate with Anterior Eye Portion: Substantially Central Position Between X and Y Scanners Coincides with Focal Position of Lens>

Figure 2:
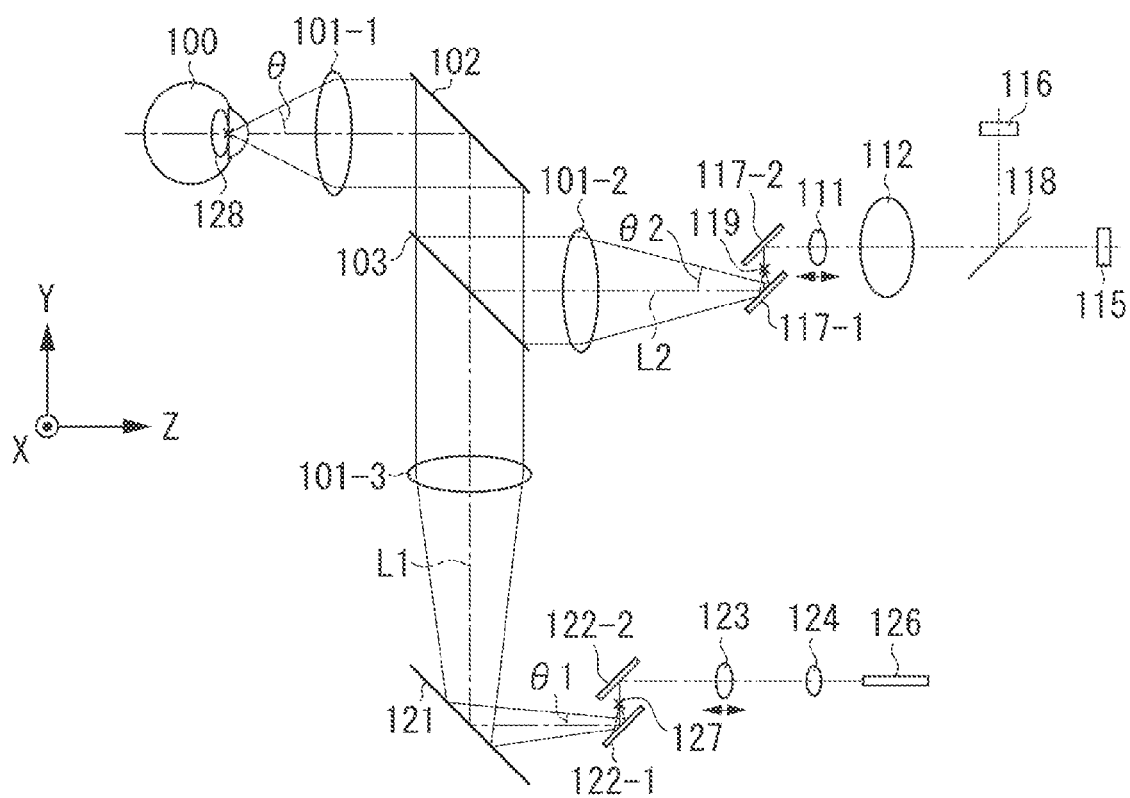
FIG. 2 illustrates exemplary optical paths of a light flux incident on a pupil of a subject's eye, in an optical tomographic imaging apparatus according to an embodiment of the present invention.

Now, conjugate relationships between the eye position and the optical path L1 and the optical path L2, and a light flux of light incident on the eye will be described with reference to FIG. 2. As illustrated in FIG. 2, the optical tomographic imaging apparatus is configured in such a manner that a predetermined portion such as the anterior eye portion of the subject's eye 100 is substantially conjugate with a position 127 located between the first scanning unit 122-1 and the second scanning unit 122-2. Similarly, the optical tomographic imaging apparatus is configured such that the anterior eye portion of the subject's eye 100 is substantially conjugate with a position 119 located between the X scanner 117-1 and the Y scanner 117-2. However, the advantages of the present exemplary embodiment can be realized as long as at least one of the optical path L1 and the optical path L2 is configured in this manner.

First, on the optical path L1, the scanner central position 127 between the X scanner 122-1 and the Y scanner 122-2, and the pupil position 128 (the anterior eye portion) of the subject's eye 100 are in an optically conjugate relationship. More specifically, the optical system of the optical head 900 is designed in such a manner that the X and Y scanners 122-1 and 122-2 configured to scan the measurement light for OCT in the X and Y directions and the anterior eye portion of the subject's eye are set in an optically conjugate relationship, when the optical head 900 and the subject's eye 100 are aligned with each other. As a result, it is possible to reduce vignetting of the measurement light on the anterior eye portion of the subject's eye 100.

Further, the lens 101-1, the lens 101-3, and the X scanner 122-1 and the Y scanner 122-2 (or the scanner central position 127) are disposed in such a manner that a light flux of the measurement light scanned by the scanning unit is substantially collimated between the lens 101-1 and the lens 101-3. According to this configuration, an optical path for which a measurement light deflection unit is set as an object point is substantially collimated between the lens 101-1 and the lens 101-3. Then, the scanner central position 127 coincides with a focal position of the lens 101-3. Due to this configuration, it is possible to substantially maintain angles at which the measurement light is incident on the first dichroic mirror 102 and the second dichroic mirror 103, even when the X scanner 122-1 and the Y scanner 122-2 scan the measurement light. As a result, even when the measurement light for OCT is scanned by the X and Y scanners 122-1 and 122-2, it is possible to reduce changes in the wavelength separation characteristics of the dichroic mirrors 102 and 103. Therefore, it is possible to improve the accuracy of wavelength separation by the dichroic mirrors 102 and 103.

Further, on the optical path L2, a scanner central position 119 between the X scanner 117-1 and the Y scanner 117-2, and the pupil position 128 of the subject's eye 100 are also in a conjugate relationship. Further, the lens 101-2 and the scanner central position 119 (half-way position between the X scanner 117-1 and the Y scanner 117-2) are disposed in such a manner that a light flux is substantially collimated between the lens 101-1 and the lens 101-2. According to this configuration, an optical path for which a measurement light deflection unit is set as an object point is substantially collimated between the lens 101-1 and the lens 101-2. Then, the scanner central position 119 coincides with a focal position of the lens 101-2. Due to this configuration, it is possible to substantially maintain angles with which the measurement light is incident on the first dichroic mirror 102 and the second dichroic mirror 103, even when the X scanner 117-1 and the Y scanner 117-2 scan the measurement light. As a result, even when the measurement light for the SLO is scanned by the X and Y scanners 117-1 and 117-2, respectively, it is possible to reduce changes in the wavelength separation characteristics of the dichroic mirrors 102 and 103. Therefore, it is possible to improve the accuracy of wavelength separation by the dichroic mirrors 102 and 103.

Further, the optical path L1 and the optical path L2 are configured to share the lens 101-1 (first lens). The structure and configuration of lens 101-1 has been discussed with reference to FIGS. 6A to 6C. To simply manufacture and ease optical calibration it is desirable that the lens 101-2 of the second optical path and the lens 101-3 of the first optical path are implemented by lenses having similar shapes and made of similar materials. An example of the structure and configuration of lens 101-3 has been described with reference to FIG. 6D. As a result, it is possible to establish matching optical systems from the subject's eye 100 to the respective X and Y scanners 122-1 and 122-2, and to X and Y scanners 117-1 and 117-2 on the optical path L1 and the optical path L2, respectively. Therefore, it is possible to establish and maintain uniform optical characteristics on the optical paths L1 and L2. Therefore, it becomes possible to reduce an error in a measurement.

Now, as illustrated in FIG. 2, assume that θ represents an angle formed by the light flux of measurement light incident on the pupil of the subject's eye 100, θ1 represents an angle formed by the light flux of measurement light incident on the scanner central position 127, and θ2 represents an angle formed by the light flux of measurement light incident on the scanner central position 119. In other words, the optical tomographic imaging apparatus is configured to provide the angles θ1 and θ2 to the light beams with use of the scanners respectively to acquire the angle θ formed by the light flux of the measurement light on both the optical path L1 and the optical path L2.

Further, as one of the optical characteristics, an optical magnification of the scanner central position 119 to the pupil position 128 and an optical magnification of the scanner central position 127 to the pupil position 128 can be made uniform on the optical path L1 and the optical path L2. That is, optical magnification of the scanner central position 127 to the pupil position 128 can be made equal to the optical magnification of the scanner central position 119 to the pupil position 128. As a result, relationships between scan angles of the X and Y scanners 122-1, 122-2, 117-1, and 117-2 on the respective optical paths L1 and L2, and illumination positions on the fundus of the subject's eye 100 can be made uniform on the optical paths L1 and L2. This means that the angles θ1 and θ2 can become substantially equal to each other. Due to this arrangement, it becomes possible to reduce an error between the respective scanning positions.

<Position Optically Conjugate with Fundus: Focusing Adjustment>

Further, the optical system of the optical head 900 is designed in such a manner that a fiber end 126 for introducing the measurement light to the measurement optical path and the fundus of the subject's eye 100 are set into an optically conjugate relationship by performing a focusing adjustment, when the X and Y scanners 122-1 and 122-2 and the anterior eye portion are in an optically conjugate relationship. The focusing lens 123 and a lens 124 are provided adjacent to the fiber end 126. Advantageously, the focusing lens 123 is driven in directions indicated by a double-headed arrow by a not-illustrated motor to perform a focusing adjustment. The focusing adjustment is performed by making an adjustment in such a manner that light emitted from the measurement light source 126, which is the fiber end, is imaged on the fundus of the subject's eye 100. The focusing lens 123, which is an example of a focusing unit, is disposed between the measurement light source 126, and the X scanner 122-1 and the Y scanner 122-2. The X scanner 122-1 and the Y scanner 122-2 are also referred to as the measurement light deflection unit. This configuration eliminates the necessity of moving the larger lens 101-3 and a fiber 125-2 connected to the measurement light source 126.

Now, for example, U.S. Pat. No. 5,537,162 discusses a configuration that maintains a constant angle as an incident angle at which a beam is incident on a dichroic mirror even when the beam is scanned by placing a beam scanner on a back focal plane of a lens (lens corresponding to the lens 101-3 in the present exemplary embodiment). Further, U.S. Pat. No. 5,537,162 discusses that the beam scanner and the lens are integrally driven during execution of a focusing adjustment for a fundus of a subject's eye. In this case, the lens (the lens corresponding to the lens 101-3 in the present exemplary embodiment) with the beam scanner placed on the back focal plane thereof tends to have a large size to introduce scanning light of the beam scanner. Therefore, a driving mechanism therefor is complicated, because the beam scanner and the large-sized lens should be integrally moved. Further, since they are integrally moved, a measurement light source in an optically conjugate relationship with a fundus position should be moved at the same time. If this measurement light source is an optical fiber end, an optical fiber should be moved, whereby a change may occur in a polarized state. Therefore, according to the present exemplary embodiment, as described above, the focusing lens 123 is disposed between the X and Y scanners 122-1 and 122-2 that scan the measurement light for OCT in the X and Y directions, and the fiber end 126 that emits the measurement light for OCT (or an optical coupler 125 that branches light into the measurement light and the reference light). If the focusing position is changed by moving the lens 101-1 in an optical axis direction, this also causes a change in the optically conjugate relationship between the X and Y scanners 122-1 and 122-2 and the anterior eye portion, whereby vignetting of the measurement light may occur on an iris of the anterior eye portion and the like.

With this focusing adjustment, an image of the measurement light source 126 can be formed on the fundus of the subject's eye 100, and the return light from the fundus of the subject's eye 100 can be efficiently returned to the fiber 125-2 via the measurement light source 126. Further, a focusing adjustment can be performed with use of a focusing lens 111 on the optical path L2 in a similar manner.

<Configuration of OCT Optical System>

Next, configurations of an optical path of light emitted from a light source 130 illustrated in FIG. 1, a reference optical system, and the spectrometer 180 will be described. A Michelson interference system is formed by the light source 130, a mirror 153, a dispersion compensation glass 152, the optical coupler 125, optical fibers 125-1, 125-2, 125-3 and 125-4, a lens 151, and the spectrometer 180. The optical fibers 125-1 to 125-4 form a single-mode optical fiber by being connected to the optical coupler 125 to be integrated all together.

The light emitted from the light source 130 is transmitted to the optical coupler 125 via the optical fiber 125-1, and is divided into the measurement light emitted to the optical fiber 125-2 and the reference light emitted to the optical fiber 125-3 via the optical coupler 125. The fundus of the subject's eye 100 is irradiated with the measurement light, which is an observation target, via the above-described optical path of the OCT optical system, and reaches the optical coupler 125 via the same optical path by being reflected or scattered by a retina.

On the other hand, the reference light reaches the mirror 153 and is reflected thereby after being transmitted via the optical fiber 125-3, the lens 151, and the dispersion compensation glass 152 inserted to match dispersion of the measurement light and dispersion of the reference light. Then, the reference light reaches the optical coupler 125 by returning through the same optical path.

The measurement light and the reference light are combined by the optical coupler 125, thereby producing interference light. Interference occurs when an optical path length of the measurement light and an optical path length of the reference light become substantially equal. The mirror 153 is held in such a manner that its position can be adjusted in the optical axis direction by a motor and driving mechanism (not-illustrated), and can match the optical path length of the reference light to the optical path length of the measurement light, which varies depending on the subject's eye 100. The interference light is guided to the spectrometer 180 via the optical fiber 125-4.

The spectrometer 180 includes a lens 181, a diffraction grating 182, a lens 183, and a line sensor 184. The interference light emitted from the optical fiber 125-4 is dispersed by the diffraction grating 182 after being substantially collimated via the lens 181, and is imaged on the line sensor 184 by the lens 183.

Next, the light source 130 will be described. The light source 130 is a super luminescent diode (SLD), which is a representative low-coherent light source. The central wavelength is 855 nm, and the wavelength bandwidth is approximately 100 nm. The wavelength bandwidth is an important parameter, because it affects a resolution of an acquired tomographic image in the optical axis direction. Further, the SLD is selected in the present example as the type of the light source, but the light source 130 may be any light source that can emit low-coherent light and can be also realized by amplified spontaneous emission (ASE) and the like. A suitable central wavelength is near infrared light in consideration of the fact that the optical tomographic imaging apparatus is used to measure a subject's eye. Further, it is desirable that the central wavelength is as a small wavelength as possible, because it affects a lateral resolution of an acquired tomographic image. For both reasons, 855 nm is selected as the central wavelength.

The present exemplary embodiment uses a Michelson interferometer as the interferometer, but it may use a Mach-Zehnder interferometer or the like, instead. It is desirable to, according to a difference in light amount between the measurement light and the reference light, use a Mach-Zehnder interferometer if their light amounts are largely different and to use a Michelson interferometer if their light amounts are relatively similar (slightly different).

<Method for Capturing Tomographic Image>

The optical tomographic imaging apparatus can capture a tomographic image of a desired portion on the fundus of the subject's eye 100 by controlling the X scanner 122-1 and the Y scanner 122-2.

Figure 3:
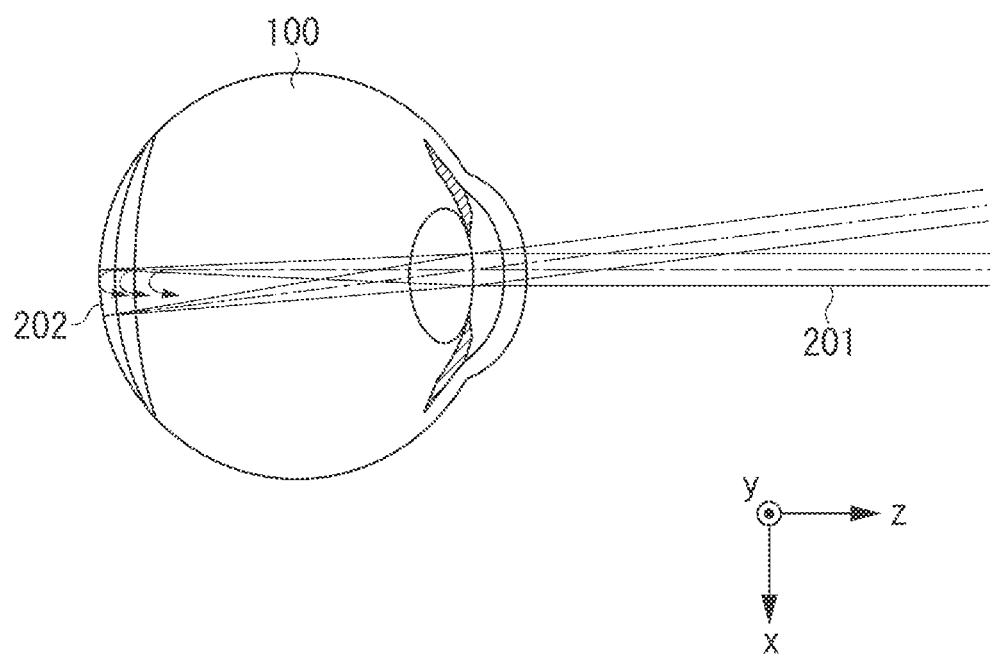
FIG. 3 illustrates an example of how measurement light is scanned on a subject's eye by an X scanner in an X direction in the optical tomographic imaging apparatus.

FIG. 3 illustrates how the subject's eye 100 is irradiated with the measurement light 201, and the measurement light 201 is scanned on a fundus 202 in the X direction. Information corresponding to a predetermined number of times of imaging is captured by from an imaging range on the fundus 202 in the X direction by the line sensor 184. Luminance distribution on the line sensor 184 that is acquired at a certain position in the X direction is transformed by fast Fourier transformation (FFT). Linear luminance distribution acquired by FFT is converted into density or color information to be displayed on a monitor, and this converted image is referred to as an A-scan image. Further, a two-dimensional image formed by arranging a plurality of A-scan images is referred to as a B-scan image. A plurality of B-scan images can be acquired by capturing a plurality of A-scan images to construct a single B-scan image, and then moving a scanning position in the Y direction and performing scanning in the X direction again. The plurality of B-scan images or a three-dimensional tomographic image constructed from the plurality of B-scan images is displayed on the monitor, whereby the examiner can use the image for a diagnosis of the subject's eye 100.

Figure 4:
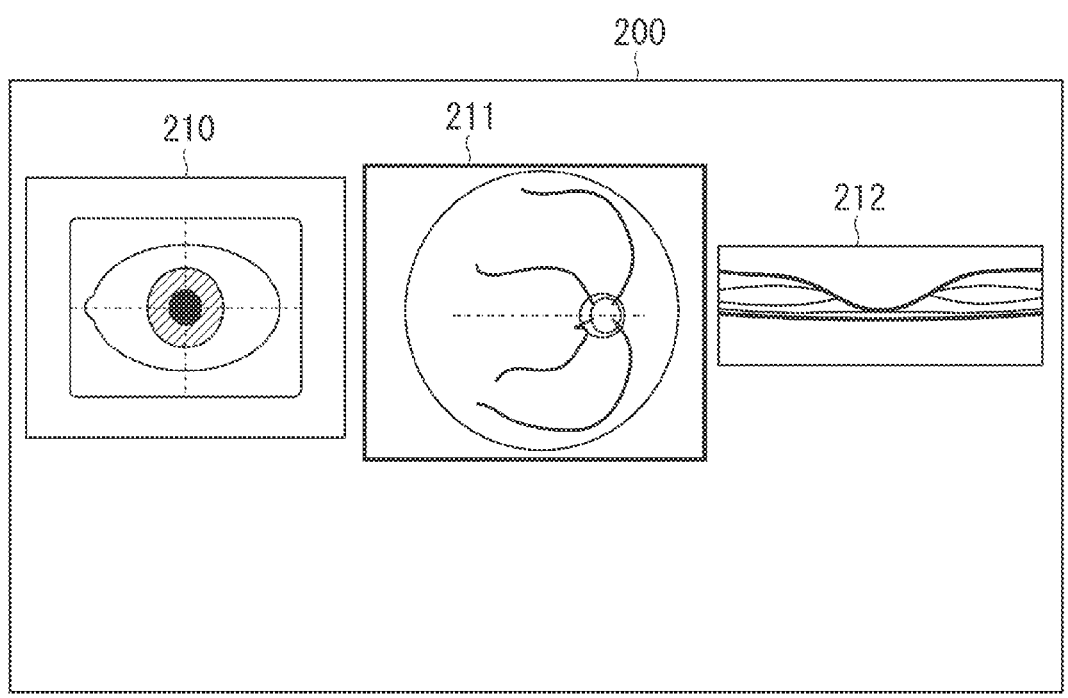
FIG. 4 illustrates exemplary representations of an image of an anterior eye, a two-dimensional image of a fundus, and a B-scan image displayed on a monitor in the optical tomographic imaging apparatus.

FIG. 4 illustrates examples of an anterior eye image 210, a fundus two-dimensional image 211, and a B-scan image 212, which is a tomographic image, displayed on a monitor 200. The anterior eye image 210 is an image processed and displayed from an output of the infrared CCD sensor 142. The fundus two-dimensional image 211 is an image processed and displayed from an output of a CCD 114. Then, the B-scan image 212 is an image constructed by performing the above-described processing from an output of the line sensor 184.

As described above, according to the present exemplary embodiment, in the optical tomographic imaging apparatus, the focusing unit (the focusing lens 123 and the not-illustrated driving mechanism) configured to perform a focusing adjustment that targets the subject's eye 100 is disposed between the measurement light deflection unit (the X and Y scanners 122-1 and 122-2) configured to deflect the measurement light, and the measurement light source 126. Further, the first lens (the lens 101-1) and the second lens (the lens 101-3) are disposed on the measurement optical path between the measurement light deflection unit (the X and Y scanners 122-1 and 122-2) and the subject's eye 100, and the optical path branching unit (the first dichroic mirror 102 and the second dichroic mirror 103) is disposed between the first lens and the second lens.

In other words, the focusing lens 123 is disposed between the fiber end 126 as the measurement light source and the X and Y scanners 122-1 and 122-2 as the measurement light deflection unit, which eliminates the necessity of moving the large lens 101-3, the fiber 125-2 connected to the measurement light source 126, and the like, leading to simplification of the driving mechanism. Further, because the fiber end 126 does not have to be moved, it is possible to provide an optical tomographic imaging apparatus capable of maintaining a polarized state. Further, according to the present exemplary embodiment, in the optical tomographic imaging apparatus, the first lens (the lens 101-1) and the second lens (the lens 101-3), and the measurement light deflection unit (the X and Y scanners 122-1 and 122-2) are positionally adjusted and arranged in such a manner that the light is collimated on the measurement optical path between the first lens (the lens 101-1) and the second lens (the lens 101-3). As a result, it is possible to maintain constant angles as the incident angles with which the beam is incident on the first and second dichroic mirrors 102 and 103, thereby improving the accuracy of wavelength separation.

The present exemplary embodiment has been described, targeting a subject's eye. However, the present invention may scan light on not only a subject's eye but also another object to be examined, like a human body such as skin and an internal organ, and can be employed for not only an ophthalmologic apparatus but also an imaging apparatus such as an endoscope.

OTHER EMBODIMENTS

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-095623 filed Apr. 30, 2013, which is hereby incorporated by reference herein in its entirety.

What is claimed is:

1. An optical tomographic imaging apparatus configured to acquire a tomographic image of an object to be examined based on light produced by combining return light from the object to be examined irradiated with measurement light via a first lens, and reference light corresponding to the measurement light, the optical tomographic imaging apparatus comprising:
 a first scanning unit disposed on an optical path of the measurement light, and configured to scan the measurement light on the object to be examined in a first direction;
 a second scanning unit disposed on the optical path of the measurement light, and configured to scan the measurement light in a second direction intersecting with the first direction;
 a second lens disposed on the optical path of the measurement light between the first lens and the first and second scanning units, the second lens having a focal length longer than a focal length of the first lens; and
 an optical path branching unit disposed between the first lens and the second lens, the optical path branching unit being configured to branch light from the optical path of the measurement light to an observation optical path for observing the object to be examined,
 wherein a focal position of the second lens is located a substantially half-way between the first and second scanning units, and
 wherein the first and second scanning units scan the measurement light with a narrower range of an angle than a range of an angle with which the measurement light irradiates the object to be examined via the first lens.

2. The optical tomographic imaging apparatus according to claim 1, wherein the first lens is a lens having an aspherical surface to reduce a spherical aberration.

3. The optical tomographic imaging apparatus according to claim 1, wherein the second lens is constructed by joining together a plurality of spherical lenses having different refractive indices.

4. The optical tomographic imaging apparatus according to claim 1, wherein the object to be examined is an eye to be examined, and
wherein the first and second scanning units are disposed at a position substantially conjugate with an anterior eye portion of the eye to be examined.

5. An optical tomographic imaging apparatus configured to acquire a tomographic image of an object to be examined based on light produced by combining return light from the object to be examined irradiated with measurement light via a first lens, and reference light corresponding to the measurement light, the optical tomographic imaging apparatus comprising:
a scanning unit disposed on an optical path of the measurement light, and configured to scan the measurement light on the object to be examined;
a second lens disposed on the optical path of the measurement light between the scanning unit and the first lens, the second lens having a focal length longer than a focal length of the first lens; and
an optical path branching unit disposed between the first lens and the second lens, and configured to branch the optical path of the measurement light to form an observation optical path for observing the object to be examined,
wherein the scanning unit is disposed at a focal position of the second lens, and
wherein the scanning unit scans the measurement light via the second lens at a smaller angle than an angle at which the measurement light irradiates the object to be examined via the first lens.

6. The optical tomographic imaging apparatus according to claim 5, wherein the object to be examined is an eye to be examined, and
wherein the scanning unit is disposed at a position substantially conjugate with an anterior eye portion of the eye to be examined.

7. An optical tomographic imaging apparatus configured to acquire a tomographic image of an object to be examined based on light produced by combining return light from the object to be examined irradiated with measurement via a first lens, and reference light corresponding to the measurement light, the optical tomographic imaging apparatus comprising:
a scanning unit disposed on an optical path of the measurement light, and configured to scan the measurement light on the object to be examined;
a second lens disposed on the optical path of the measurement light between the scanning unit and the first lens, the second lens having a longer focal length than a focal length of the first lens; and
an optical path branching unit disposed between the first lens and the second lens, and configured to branch the optical path of the measurement light to form an observation optical path for observing the object to be examined,
wherein the first lens includes an aspherical surface and the second lens includes a plurality of spherical lenses joined together.

8. The optical tomographic imaging apparatus according to claim 7, wherein the object to be examined is an eye to be examined, and
wherein the scanning unit is disposed at a position substantially conjugate with an anterior eye portion of the eye to be examined.

* * * * *